United States Patent [19]

McClure

[11] Patent Number: 5,087,557

[45] Date of Patent: Feb. 11, 1992

[54] HUMAN MONOCLONAL ANTIBODY TO LYMPHADENOPATHY-ASSOCIATED VIRUS

[75] Inventor: Janela McClure, Vashon Island, Wash.

[73] Assignee: Genetic Systems Corporation, Redmond, Wash.

[21] Appl. No.: 498,454

[22] Filed: Mar. 19, 1990

Related U.S. Application Data

[63] Continuation of Ser. No. 877,579, Jun. 23, 1986, abandoned.

[51] Int. Cl.$^5$ ............................................ G01N 33/569
[52] U.S. Cl. ............................................. 435/5; 435/7.2; 435/70.21; 435/240.27; 435/974; 436/811; 436/548; 530/387
[58] Field of Search ................ 530/387; 435/5, 172.2, 435/240.27, 7.2, 70.21, 974; 436/504, 511, 548, 811

[56] References Cited

U.S. PATENT DOCUMENTS

| | | | |
|---|---|---|---|
| 4,464,465 | 8/1984 | Lostrom | 435/68 |
| 4,629,783 | 12/1986 | Cosand | 530/324 |
| 4,720,459 | 1/1988 | Winkelhake | 435/240.2 |
| 4,761,377 | 8/1988 | Glassy et al. | 435/240.27 |
| 4,772,547 | 9/1988 | Heimer et al. | 435/5 |
| 4,784,941 | 11/1988 | Watanabe et al. | 435/5 |
| 4,904,581 | 2/1990 | Burger et al. | 435/5 |

FOREIGN PATENT DOCUMENTS

| | | | |
|---|---|---|---|
| 5636386 | 10/1986 | Australia | 435/5 |
| 6399786 | 4/1987 | Australia | 435/5 |
| 185444 | 6/1986 | European Pat. Off. | 435/5 |
| 214709 | 3/1987 | European Pat. Off. | 435/5 |
| 8606414 | 11/1986 | World Int. Prop. O. | 435/5 |

OTHER PUBLICATIONS

Veronese et al., *Proc. Natl. Acad. Sci. USA* 82:5199 (1985).
Chassagne et al., *J. Immunol.* 136:1442 (1986).
Veronese et al., Science vol. 229, pp. 1402-1404, 1985.
Kipps et al., In Applications of Immunologized Methods in Biomedical Sciences, vol. 4, Edited by D. M. Weis, Black Well Scientific Publishers, 1986.

*Primary Examiner*—Christine Nucker
*Attorney, Agent, or Firm*—Townsend and Townsend

[57] ABSTRACT

Human monoclonal antibodies capable of specifically reacting with an antigenic determinant of LAV/HTLV-III and cell lines producing those monoclonal antibodies are disclosed. The human monoclonal antibodies may be utilized in a method for determining the presence of LAV/HTLV-III in biological samples, or in a method for separating specific antigenic determinants of LAV/HTLV-III from a mixture. Pharmaceutical compositions containing such a human monoclonal antibody, and a method for significantly reducing the infectivity of LAV/HTLV-III in animals using the composition are also disclosed.

18 Claims, 2 Drawing Sheets

ENV-3

```
          #5
Ile Phe Arg Pro Gly Gly Gly Asp Met Arg Asp Asn Trp Arg Ser Glu

30
Leu Try Lys Tyr Lys Val Val Lys Ile Glu Pro Leu Gly Val Ala Pro

#2           40
Thr Lys Ala Lys Arg Arg Val Val Gln Arg Glu Lys Arg Ala Val Gly

50          #1                        60
Ile Gly Ala Leu Phe Leu Gly Phe Leu Gly Ala Ala Gly Ser Thr Met 70                                        80
Gly Ala Gly Ser Met Thr Leu Thr Val Gln Ala Arg Gln Leu Leu Ser

90
Gly Ile Val Gln Gln Asn Asn Leu Leu Arg Ala Ile Glu Ala Gln 100                              110
Gln His Leu Leu Gln Leu Thr Val Trp Gly Ile Lys Gln Leu Gln Ala

120
Arg Ile Leu Ala Val Glu Arg Tyr Leu Lys Asp Gln Gln Leu Leu Gly

130              #3              140
Ile Trp Gly Cys Ser Gly Lys Leu Ile Cys Thr Thr Ala Val Pro Trp 150                              160
Asn Ala Ser Trp Ser Asn Lys Ser Leu Glu Gln Ile Trp Asn Asn Met

170    #4
Thr Trp Met Glu Trp Asp Arg Glu Ile Asn Asn Tyr Thr
```

FIG. 2 ns immunological techniques to provide novel materials useful in diagnosing and treating viral infections as well as useful in biochemical and histological studies. More particularly, the present invention relates to the production and characterization of human monoclonal antibodies capable of reacting with the lymphadenopathy associated virus, LAV/HTLV-III.

HUMAN MONOCLONAL ANTIBODY TO LYMPHADENOPATHY-ASSOCIATED VIRUS

DESCRIPTION

1. Technical Field

The present invention relates generally to the use of immunological techniques to provide novel materials useful in diagnosing and treating viral infections as well as useful in biochemical and histological studies. More particularly, the present invention relates to the production and characterization of human monoclonal antibodies capable of reacting with the lymphadenopathy associated virus, LAV/HTLV-III.

2. Background Art

Acquired Immune Deficiency Syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, known as Lymphadenopathy-Associated Virus (LAV) (Barre-Sinoussi et al., *Science* 225:840 (1984) and designated Human T-cell Lymphotropic Virus (HTLV-III), AIDS-Associated Retrovirus (ARV), Immune Deficiency-Associated Virus (IDAV), or human immunodeficiency virus (HIV). Still more recent data indicate that LAV, HTLV-III, ARV, and IDAV share several important characteristics, including substantial nucleotide homology (Wain-Hobson et al., *Cell* 40:9 (1985); Muesing et al., *Nature* 313:450 (1985); Sanchez-Pescador et al., *Science* 227:484 (1985), and should be considered isolates of the same virus, although there is a likelihood that strain-to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, Supra; Schupbach et al., Science 224:503 (1984).

The transmissibility of the AIDS virus through blood products (blood, blood serum, blood plasma, and fractions thereof) makes it important to screen the blood products to determine if donors have been exposed to the virus and are potential carriers. Several products that use disrupted viral antigen in ELISA formats are currently being marketed for this purpose. Individuals whose blood contains antibodies to LAV/HT LV-III are said to be "seropositive." Blood from these seropositive donors may be eliminated from the blood supply upon detection, thereby helping to prevent the spread of the disease.

The lack of antibody response to LAV/HTLV-IIT is not always indicative of lack of infectivity of blood products. Virus has been cultured from blood samples collected from individuals found to be antibody negative and showing no signs of clinical manifestations (Salahuddin, S. Z., et al., *Lancet* ii:1418 (1984)). There is a need in the art for an antigen capture assay system to prevent these infective, antibody negative blood products from entering into the blood supply. Monoclonal antibodies reactive with major viral components may provide the basis for such a system of antigen detection.

Recently there has been a report of murine monoclonal antibodies reactive with the p24 core protein of LAV/HTLV-III and its protein precursors and a murine antibody reactive with the envelope glycoprotein gp41. (di Marzo Veronese et al. *Proc. Natl. Acad. Sci. USA* 82:5199 (1985); di Marzo Veronese et al., *Science* 229:1402 (1985). Chassagne et al. (*J. Immunol.* 136:1442 (1986)) have also described a murine monoclonal antibody specific for p24 and its precursors. These antibodies have been used experimentally to trace the processing of core protein precursors in infected cells to final viral proteins.

Although it is possible to detect antibody-positive individuals and may be possible to detect those antigen-positive, no effective treatment or preventative measure for the disease have yet been found. With the spread of AIDS beginning to reach extraordinary, if not epidemic proportions, and the extent to which the virus may be transmitted still in question, there is a need in the art for a composition with prophylactic and/or therapeutic effects.

DISCLOSURE OF INVENTION

Briefly stated, the present invention discloses (1) human monoclonal antibodies capable of reacting with an antigenic determinant of LAV/HTLV-III; (2) immortalized cell lines that produce these human monoclonal antibodies; and (3) methods for utilizing the human monoclonals, for instance, in determining the presence of LAV/HTLV-III in biological samples. Another method described herein includes a procedure for separating specific antigenic determinants of LAV/HTLV-III from a mixture. Further, pharmaceutical compositions are disclosed which comprise a therapeutically effective amount of a human monoclonal antibody capable of reacting with an antigenic determinant of LAV/HTLV-III, and a physiologically acceptable carrier and/or diluent. Compositions having this characteristic are particularly useful within a method for significantly reducing the infectivity of LAV/HTLV-III in warm-blooded animals.

As noted above, one aspect of the present invention provides a method for determining the presence of LAV/HTLV-III in a biological sample. The method generally involves (a) incubating a human monoclonal antibody capable of reacting with an antigenic determinant of LAV/HTLV-III with a biological sample; and (b) detecting the presence of immunecomplexes formed between the monoclonal antibody and the biological sample, and therefrom determining the presence of LAV/HTLV-III. Labeled or unlabeled monoclonal antibodies may be used. The method is applicable to detecting LAV/HTLV-III in a wide variety of biological samples, including bodily secretions, bodily fluids, and tissue specimens.

Another aspect of the present invention, as noted above, provides a method for separating specific antigenic determinants of LAV/HTLV-III from a mixture containing antigenic determinants of LAV/HTLV-III. The method comprises (a) immobilizing a human monoclonal antibody capable of reacting with the specific antigenic determinants on a substrate; (b) contacting the mixture containing the LAV/HTLV-III antigenic determinants with the immobilized antibody under suitable conditions such that immunecomplexes are formed between the antibody and the specific antigenic determinants; and (c) separating the immunecomplexes from the mixture.

Other aspects of the invention will become evident upon reference to the following detailed description and attached drawings.

BRIEF DESCRIPTION OF THE DRAWINGS.

FIG. 2 illustrates the amino acid sequence of ENV-3.

BEST MODE FOR CARRYING OUT THE INVENTION

Figure 1:
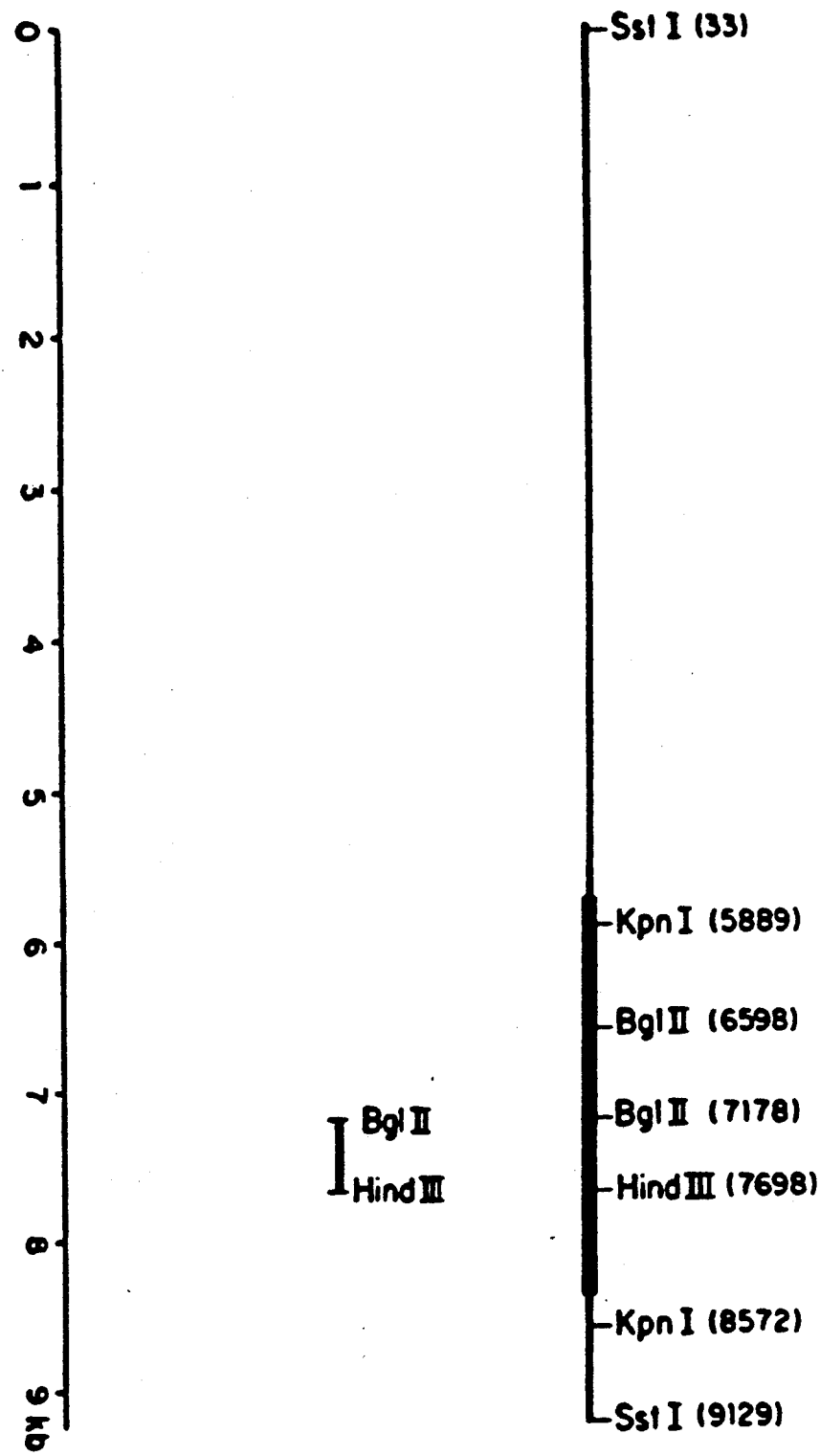
FIG. 1 illustrates the origin of the LAV inserts in pENV-3.

Prior to setting forth the invention, it may be helpful to an understanding thereof to set forth definitions of certain terms to be used hereinafter.

Lymphadenopathy-Associated Virus (LAV): A human T-lymphotropic retrovirus. For purposes of the present invention, a virus is considered to be the same as or equivalent to LAV if it substantially fulfills the following criteria:

(a) the virus is tropic for T-lymphocytes, especially T-helper cells (CD4+, according to the international nomenclature defined in Bernard et al., eds., *Leucocyte Typing*, New York: Springer Verlag (1984));

(b) the virus is cytopathic for infected CD4+ cells (rather than transforming, as are HTLV-I and II);

(c) the virus encodes an RNA-dependent DNA polymerase (reverse transcriptase) which is $Mg^{2+}$-dependent (optimum concentration 5 mM, optimum pH 7.8, not inhibitable by actinomycin D) and can employ $(dT)_{12-18}$ as a primer for reverse transcription from its 3' LTR;

(d) the virus bands in a sucrose gradient at a density of approximately 1.16;

(e) the virus can be labeled with [$^3$H] uridine;

(f) the virus is distinct by immunological and nucleotide sequence criteria from members of the HTLV-I/II family of viruses (by this criterion HTLV-III is not to be considered a member of the HTLV-I/II family);

(g) the virus is substantially cross-reactive immunologically with proteins encoded by the gag and env regions of LAV; and (h) the virus shares substantial nucleotide homology (78-100%) and amino acid sequence homology (90-100%) with LAV.

The Human Retrovirus Subcommittee of the International Committee on the Taxonomy of Viruses has recommended the designation of Human Immunodeficiency Virus (HIV) (*Science* 232:697 (1986)), therefore, for purposes of the present invention, LAV/HTLV-III and HIV are considered to be equivalent.

In accordance with the present invention, a novel hybrid cell is provided for the specific recognition of the proteins and protein precursors of the human imunodeficiency virus, LAV/HTLV-III. The subject cells have an identifiable chromosome, in which the germ line DNA has rearranged to encode an antibody having a binding site for an epitope common to some or all the human immunodeficiency virus clinical isolates, but not found on other human retroviruses, such as HTLV-I and HTLV-II. These human monoclonal antibodies can be used in a wide variety of ways, including diagnosis and therapy.

The preparation of monoclonal antibodies can be accomplished by immortalizing the expression of nucleic acid sequences that code for antibodies specific for an epitope on antigens of LAV/HTLV-III. Typically the monoclonal antibodies are produced by cell-driven Epstein-Barr virus (EBV) transformation of B-lymphocyte cells obtained from human donors who are or have been exposed to LAV/HTLV-III. The antibody secreting cell lines so produced are characterized as continuously growing lymphoblastoid cells that possess a diploid karyotype, are Epstein-Barr nuclear antigen positive, and secrete monoclonal antibody of either IgG, IgM, IgA, or IgD isotype, including various subtypes such as IgG1, IgG2, IgG3 and IgG4. The cell-driven transformation process itself is described in detail in U.S. Pat. No. 4,464,465, which is incorporated herein by reference. The monoclonal antibodies may be used intact, or as fragments, such as Fv, Fab, F(ab')$_2$, but usually intact.

Alternatively, cell line s producing the antibodies could be produced by cell fusion between suitably drug-marked human myeloma, mouse myeloma, or human lymphoblastoid cells with human B-lymphocytes to yield human hybrid cell lines.

The cell line of the present invention may find uses other than for the direct production of the human monoclonal antibodies. The cell line may be fused with other cells (such as suitably drug-marked human myeloma, mouse myeloma or human lymphoblastoid cells), to produce hybridomas, and thus provide for the transfer of genes encoding the monoclonal antibodies. Alternatively, the cell line may be used as a source of the chromosomes encoding the immunoglobulins, which may be isolated and transferred to cells by techniques other than fusion. In addition, the genes encoding the monoclonal antibodies may be isolated and used in accordance with recombinant DNA techniques for the production of the specific immunoglobulin in a variety of hosts. Particularly, by preparing cDNA libraries from messenger RNA, a single DNA clone, coding for the immunoglobulin and free of introns, may be isolated and placed into suitable prokaryotic or eukaryotic expression vectors and subsequently transformed into a host for ultimate bulk production.

The lymphoblastoid or hybrid cell lines may be cloned and screened in accordance with conventional techniques, and antibodies in the cell supernatants detected that are capable of binding to the LAV/HTLV-III viral proteins, recombinant fusion proteins, or synthetic peptides. The appropriate hybrid cell lines may then be expanded in vitro or injected into the peritoneal cavity of an appropriate host for production of ascites fluid. By virtue of having the antibody of the present invention, which is known to be specific for the LAV/HTLV-III virus, the supernatants may be screened in competition with the subject monoclonal antibodies in a competitive assay. Thus, hybrid cell lines can be readily produced from a variety of sources based on the availability of the present antibodies specific for the particular antigen.

The monoclonal antibodies of the present invention are particularly useful because of their specificity for gp41, expressed fusion proteins and synthetic antigens of LAV/HTLV-III from the envelope region.

The monoclonal antibodies can also find a wide variety of utilities in vitro. By way of example, the monoclonal antibodies can be utilized for assaying whether virus is present in infected cultured lymphocytes by indirect immunofluorescence. Viral proteins or portions of viral proteins can be removed from disrupted purified viral preparation or from complex mixtures of which these proteins are constituents.

These specific viral proteins can be removed by attachment of the monoclonal antibodies to a support material such as polymeric tubes, beads, polysaccharide particulates and the like. Methods of attachment are well known in the art, see for example Schall and Tenoso, *Immunoassays: Clinical Laboratory Techniques for the 1980's*: 127 (1980) Alan R. Liss Inc. Mixtures are combined with the immobilized antibody under conditions which will allow binding to occur. Immune-complexes are separated from the rest of the mixture by methods appropriate for the support. These methods are well known in the art. Isolated viral proteins can then be released from the antibody by use of conditions unfavorable to immune-complex formation.

For diagnostic purposes, the monoclonal antibodies may either be labeled or unlabeled. Typically, diagnostic assays entail the detection of the formation of a complex through the binding of the monoclonal antibody to the LAV/HTLV-III antigen. When unlabeled, the antibodies find use in agglutination assays. In addition, unlabeled antibodies can be used in combination with other labeled antibodies (second antibodies) that are reactive with the monoclonal antibody, such as antibodies specific for immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some include those described in U.S. Pat. Nos. 3,817,827; 3,850,752; 3,901,654; 3,935,074; 3,984,533; 3,996,345; 4,034,074; and 4,098,876, all of which are herein incorporated by reference.

Commonly, the monoclonal antibodies of the present invention are utilized in enzyme immunoassays, where the subject antibodies, or second antibodies from a different species, are conjugated to an enzyme. When a biological sample containing LAV/HTLV-III antigens, such as human blood serum or viral cell culture supernatant, is combined with the subject antibodies, binding occurs between the antibodies and those molecules exhibiting the desired epitope. Such proteins or viral particles may then be separated from the unbound reagents, and a second antibody (labeled with an enzyme) added. Thereafter, the presence of the antibody-enzyme conjugate specifically bound to the antigen is determined. Other conventional techniques well known to those skilled in the art may also be utilized.

Kits can also be supplied for use with the subject antibodies in the detection of LAV/HTLV-III infection or for the presence of LAV/HTLV-III antigen. Thus, the subject monoclonal antibody composition of the present invention may be provided, usually in a lyophilized form, either alone or in conjunction with additional antibodies specific for other epitopes of LAV/HTLV-III. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

As indicated previously, the detection of antigen is useful in diagnosing present infection by the LAV/HTLV-III virus. The presence of the virus in various biological samples can also be accomplished. Biological samples can include, but are not limited to, blood serum, saliva, semen, tissue biopsy samples (brain, skin, lymphnodes, spleen, etc.), cell culture supernatants, disrupted viral and bacterial expression systems and the like. Presence of virus is tested for by incubating the human monoclonal antibody with the biological sample under conditions conducive to immunecomplex formation, followed by the detection of complex formation. In one embodiment, complex formation is detected through use of a second antibody capable of binding to the monoclonal antibody which is typically conjugated to a label and formulated in an analogous manner with the antibody formulations described above.

Those skilled in the art will realize that the monoclonal antibodies of the present invention will also find use in numerous additional ways, such as affinity chromatography, purification of various naturally occurring LAV/HTLV-III antigens, as well as expressed from various expression systems (i.e., *E. coli*, vaccinia, chinese hampster ovary cells, and others), histological staining reagents, and the like. See, generally, *Immunological Methods*, Vols. I and II, Eds. Lefkovits, I. and Pernis, V., Academic Press, New York (1979 and 1981); and *Handbook of Experimental Immunology*, Ed. Weir, D., Blackwell Scientific Publications, St. Louis, Mo. (1978), both of which are incorporated herein by reference.

Therapeutically, antibodies with proper biological properties are useful directly as therapeutic agents. Alternatively, the antibodies can be bound to a toxin to form an immunotoxin or a radioactive material or drug to form a radiopharmaceutical or pharmaceutical. Methods for producing immunotoxins and radiopharmaceuticals of antibodies are well known (see, for example, *Cancer Treatment Reports* 68:317 (1984)). The conjugated antibodies are mixed with physiologically acceptable carriers, such as sterile water, saline, buffered saline. Adjuvants can also be employed, such as aluminum hydroxide.

Other features and advantages of the present invention will become apparent from the following experimental descriptions, which describe the invention by way of example. This example is offered by way of illustration and not by way of limitation.

EXAMPLE

This example demonstrates methods for the production of human monoclonal antibodies that react with LAV viral proteins and characterization of those antibodies using synthetic peptides and bacterially expressed fusion proteins in immunoblots and enzyme-linked immunoassays.

A peripheral blood sample obtained from a healthy AIDS positive blood donor served as a source of human B cells. Mononuclear cells were separated from the blood by standard centrifugation techniques on Ficoll-Paque and washed twice in calcium/magnesium-free phosphate buffered saline (PBS).

The mononuclear cells were depleted of T-cells using a modified F-rosetting procedure. Briefly, the cells were first resuspended to a concentration of $1 \times 10^7$ cells/ml in PBS containing 20% fetal calf serum (FCS) at 4° C. One ml of this suspension was then placed in a 17×100 mm polystyrene round bottom tube to which was added 1×10$^9$ 2-amino-isothioronium bromide (AFT)-treated sheep red blood cells from a 10% (v/v) solution in Iscove's modified Dulbecco's medium (Iscove's medium). The suspension was very gently mixed for 5-10 minutes at 4° C. and the F-rosetted cells then removed by centrifugation on Ficoll-Paque for 8 minutes at 2500×g at 4° C. F-rosette negative peripheral blood mononuclear cells (E-PBMC) banding at the interface were collected and washed once in Tscove's medium and resuspended in same containing 15% (v/v) FCS, L-glutamine (2mmol/l), penicillin (100 IU/ml), streptomycin (100 ug/ml), hypoxanthine ($1 \times 10^{-4}$M), aminopterin ($4 \times 10^{-7}$M), and thymidine ($1.6 \times 10^{-5}$M). This medium is hereafter referred to as HAT medium.

Cell-driven transformation of the E$^-$PBMC was accomplished by co-cultivating these cells with a transforming cell line. The transforming cell line was an Epstein-Barr nuclear antigen (EBNA) positive human lymphoblastoid cell line derived by ethyl methane-sulphonate (EMS) mutagenesis of the GM 1500 lymphoblastoid cell line followed by selection in the presence of 30 ug/ml 6-thioguanine to render the cells hypoxanthine-guanine phosphoribosyl transferase (HGPRT) deficient and thus HAT sensitive. This cell line is denominated by the 1A2 cell line and was deposited at the American Type Culture Collection (A.T.C.C.) on Mar. 29, 1982, under A.T.C.C. No. CRL 8119. 1 A2 cells in logarithmic growth phase were suspended in HAT medium and then combined with the E$^-$PBMC. The cell mixture was plated into eight round-bottom 96-well microtiter plates (Costar 3799) at a concentration of 72,000 cells/well in a volume of 200 ul per well, and incubated at 37° C. in a humidified atmosphere containing 6% $CO_2$. Cultures were fed on days 5 and 8 post-plating by replacement of half the supernatant with fresh HAT medium. The wells were observed every other day on an invert ed microscope for signs of cell proliferation. Fourteen days post plating, it was observed that 100% of the wells contained proliferating cells and that by day 21 most of the wells, contained cells of sufficient density for removal and testing of supernatants for anti-LAV antibody.

Supernatants were screened for the presence of anti-LAV antibody using standard ELISA technique.

Briefly, Immulon II plates (Dynatech) were coated with disrupted whole virus in carbonate/bicarbonate buffer pH 9.6 and incubated Overnight at 4° C. Rinsed with phosphate buffered saline 0.05% Tween 20 (PBS-Tween) and then blocked with Blotto (PBS, pH 7.2, containing 5% (w/v) non-fat dry milk, 0.01% (v/v) antifoam A (Sigma), and 0.01% (w/v) Thimerosal for 60 minutes at room temperature. The plates were then rinsed three times with PBS-Tween and allowed to dry. Supernatants from wells with growing clones were added to the coated, blocked plates and incubated at 37° C. for 45 minutes, followed again by washing three times with PBS-Tween. Peroxidase-goat anti-human IgG (1:2,000 dilution in PBS-Tween, Antibodies Inc.), was added (10 ul/well). Incubation was for 45 minutes at 37° C. and washed as above. Enzyme substrate, O-phenylenediamine and hydrogen peroxide, was added and plates were incubated for 30 minutes at room temperature in the dark. The reactions were stopped with 3N $H_2SO_4$ and quantitated using an automated microplate reader.

Analysis of the culture supernatants led to the identification of one well (LT1/41-H1) which contained anti-LAV antibodies. This supernatant was further characterized by immunoblot, immunoprecipitation and ELISA with fusion proteins. The antibodies from this clone were found to be reactive with gp41 by blot and ENV-3, peptide 39 and peptide 79 by ELISA. Cell line LT1/41-H1 has been deposited with the American Type Culture Collection, 12301 Parklawn Drive, Rockville, Md. 20852 under Accession No. CRL-9128.

These antigens are important because they are from a region of LAV/HTLV-III which is consistently recognized by serum from antibody positive donors and is present throughout the course of the disease (Sarngadharan et al., *Science* 224:506 (1984); Safai et al., *Lancet* 1984-I, 1438 (1984).

The protein ENV-3 is a bacterially expressed fusion protein from pENV-3 (ATCC accession #53072) which is a region of LAV from base pair 7178 to 7698 (numbering according to Wain-Hobson et al., *Cell* 44:9 (1985)) (FIGS. 1 and 2).

Peptide 39 is a synthetic polypeptide defined as encoding the region from about base pair 7516 through 7593 and has the following amino acid sequence, where oligopeptides included within the following sequence will include linear epitopes within such sequence:

ARG—ILE—LEU—ALA—VAL—GLU—ARG—TYR—LEU—LYS—ASP—GLN—GLN—LEU—LEU—GLY—ILE—TRP—GLY—CYS—SER—GLY—LYS—LEU—ILE—CYS—X, where X is OH or $NH_2$ Table 1 depicts a comparison of peptide 39 with whole virus lysate in an ELISA for the detection of antibodies to LAV/HTLV-III.

TABLE 1

COMPARISON OF PEPTIDE 39 WITH WHOLE VIRUS LYSATE IN AN ELISA ASSAY FOR THE DETECTION OF ANTIBODIES TO LAV

| Positive Sera | Diagnosis | ELISA Using Whole Virus Lysate[1] | Confirmed as Seropositive[2] | Pep 39 |
|---|---|---|---|---|
| 155 | LAS[3] and/or homosexual | 1.069 | yes | 1.167 |
| 124 | LAS and/or homosexual | 1.189 | yes | 1.073 |
| 138 | LAS and/or homosexual | 1.302 | yes | 0.514 |
| 133 | LAS and/or homosexual | 1.250 | yes | 1.036 |
| 134 | LAS and/or homosexual | 1.050 | yes | 1.691 |
| 153 | LAS and/or homosexual | 2.000 | yes | 1.314 |
| 157 | LAS and/or homosexual | 1.349 | yes | 1.326 |
| Y-1/ | LAS and/or homosexual | 2.000 | yes | 1.305 |
| 501 | LAS and/or homosexual | 1.109 | yes | 1.167 |
| 1892 | Healthy heterosexual | n.d. | n.d.[4] | 0.045 |
| 639 | Healthy | 0.123 | not | 0.038 |

TABLE 1-continued
COMPARISON OF PEPTIDE 39 WITH WHOLE VIRUS LYSATE IN AN ELISA ASSAY FOR THE DETECTION OF ANTIBODIES TO LAV

| Positive Sera | Diagnosis | ELISA Using Whole Virus Lysate[1] | Confirmed as Seropositive[2] | Pep 39 |
|---|---|---|---|---|
| | heterosexual | | seropositive | |

[1] Prepared as described in U.K. application Ser. No. 83/24800, filed September 15, 1983.
[2] Radiolabeled LAV antigens were disrupted in RIPA buffer (Gilead et al., Nature (1976) 264:263) and then were reacted with human serum. The resultant immune complexes were separated by binding to a *Staphylococcus aureus* adsorbent (Kessler, J. Immunology (1975) 115:1617) followed by multiple washings. Immune-precipitated antigens were analyzed by SDS polyacrylamide gel electrophoresis (Laemmli, Nature (1970) 227:680) followed by fluorography. Presence of either a p25 or gp43 band was considered necessary and sufficient to confirm a sample as seropositive.
[3] LAS = lymphadenopathy syndrome.
[4] N.D. = not determined.

Peptide 79 is defined as encoding the region from about base pair 7543 through 7593 and includes any oligopeptides coding for linear epitopes within the following amino acid sequence:

Y—LYS—ASP—GLN—GLN—LEU—LEU—GLY—ILE—TRP—GLY—CYS—SER—GLY—LYS—LEU—ILE—CYS—X, wherein X is OH or $NH_2$ and Y is TYR or CYS.

Table 2 depicts the results of an ELISA for the detection of antibodies to LAV/HTLV-III using peptide 79.

TABLE 2
PEPTIDE 79 IN AN ELISA ASSAY FOR THE DETECTION OF ANTIBODIES TO LAV

| Serum No. | Confirmed as Seropositive | 79 |
|---|---|---|
| 127 | yes | 2.346 |
| 130 | yes | 1.808 |
| 124 | yes | 1.086 |
| 125 | yes | 2.266 |
| 128 | yes | 1.144 |
| 134 | yes | 1.316 |
| 135 | yes | .381 |
| 153 | yes | 1.039 |
| 154 | yes | ND |
| 155 | yes | 1.584 |
| 157 | yes | 1.162 |
| 120 | yes | 1.546 |
| 121 | yes | 2.084 |
| 132 | yes | 1.386 |
| 138 | yes | .312 |
| 133 | yes | .597 |
| 131 | yes | 1.150 |
| 501 | yes | 1.768 |
| 129 | yes | .562 |
| Y1 | yes | ND |
| N3 | no | .224 |
| N12 | no | .174 |
| N4 | no | .172 |
| 639 | no | .153 |
| 641 | no | .140 |
| N13 | no | .226 |
| N14 | no | .162 |
| N16 | no | .183 |
| Cutoff | | 0.30 |
| Fraction of Confirmed Seropositive samples detected as positive | | 18/18 |

Western Blotting

Characterization by Western immunoblotting was carried out on clone supernatants using purified LAV virus and recombinant fusion proteins as antigens. These antigens were first separated by gradient gel electrophoresis (7.0–15.0%) and transferred to nitrocellulose membrane (NCM) by electrophoresis for four hours at 25 V in 25 mM sodium phosphate (pH 7.0). After transfer, the NCM was blocked in PBS-Tween for one hour at room temperature. The NCM was incubated with goat anti-human IgG-Horse radish peroxidase diluted in PBS-Tween for one hour at room temperature. This was followed by washing in PBS-Tween and then immersion in horse radish peroxidase color development solution (Bio-Rad Laboratories, Richmond, Calif.) for 20 minutes. The reaction was stopped by immersion in deionized water. Monoclonal antibody reactivity was compared to a standard positive serum reaction with purified disrupted virus run as a positive control.

Immunoprecipitation

Viral extracts for radioimmune precipitation were prepared from CEM cells (ATCC #CCL119) infected with the LAV 1 isolate of LAV/HTLV-III adapted to lytic growth by continuous passage in tissue culture. When early cytopathic effect was evident, the cells were transferred to labeling media containing $^{35}$[S] methionine (50 uCi/ml) or $^3$[H] glucosamine (25 uCi/ml), then incubated for 24 h until most of the cells had lysed, releasing virus into the culture supernatant. Virus was pelleted (one hour at 100,000×g) from the cell-free culture supernatant, and detergent extracts were prepared in P-RIPA buffer (phosphate buffered saline containing 1.0% Triton X-100, 1.0% dedxycholic acid, 0.1% SDS, and 1.0% aprotinin). Similar extracts were prepared from uninfected cells after washing once in PBS. Immunoprecipitation assays were performed with 100 ul extract volume incubated with culture supernatant for 1 h on ice. Immunoprecipitin (100 ul; BRL) resuspended in P-RIPA containing 1.0% ovalbumin, was added to each tube and incubated for an additional 30 minutes. The bound complexes were washed and separated by SDS-PAGE (7.0–15.0% gradient gel). Following electrophoresis, the cells were fixed, soaked in Enhance (NEN), dried, and exposed to Kodak EX-5 film.

A reference positive serum which immunoprecipitated all LAV/HTLV-III viral protein was reacted with $^{35}$[S]methionine-labeled extract from culture supernatant of mock-infected cells and with $^{35}$[S]methionine-labeled viral extract as a positive and negative control.

Enzyme-Linked Immunosorbent Assay

The antibody LT1/41-H1 was further characterized by ELISA. Methods are as described above except bacterially expressed fusion proteins and synthetic peptides are used in place of disrupted whole virus as antigen.

Indirect Immunofluorescence Assay

Indirect immunofluorescence assays were carried out on acetone fixed and live cells. Acetone fixed slides prepared from LAV-infected CEM cells were incubated with culture supernatant for one hour at 37° C. while live cells were incubated with culture supernatant for one hour at 4° C. before the cells were plated and fixed. In both methods, reactive cells were detected with fluorescein isothiocyanate-labeled anti-human IgG (Antibodies Inc.).

Neutralization assays were carried out on the monoclonal antibody by serial dilution of virus into 100 ul of antibody supernatant or control serum. A set of 1:5 dilutions of virus was prepared using a 96 well microtiter plate. Tested with the LT1/41-H1 antibody were heat inactivated LAV seropositive serum with known neutralizing activity (1:10 dilution in medium), heat inactivated normal human serum (1:10 dilution in medium), supernatant from an irrelevant human monoclonal antibody producing cell line, and a medium control. These preparations were filtered with 0.45 u filter before use. A viral concentration of approximately $2.5 \times 10^4$ tissue culture infective does (TCID) was used to start the serial dilution. Antibody and virus were incubated for one hour at 37° C. A second 96 well plate was prepared with CEM-F cells plated at $1 \times 10^5$ cells/well in 150 ul, followed by inoculation with 50 ul/well (about $1 \times 10^4$ TCID in first column) of the antibody-virus mixture. The second plate was incubated at 37° C. for 24-48 hours, at which time all of the supernatant was removed. Fresh medium (200 ul) was added and the plate was incubated for an additional 7-14 days with refeeding every 24-48 hours. On days 7, 10, and 14 the cells are harvested and assayed for virus expression by immunofluorescence.

Cloning of specific antibody producing cells from well LT1/41-H1 was accomplished by subjecting the cells to several rounds of limiting dilution cloning until all clonal supernatants assayed by the above methods resulted in antibodies which were able to immunoblot and immunoprecipitate gp41 and gave positive reactions with pENV-3, peptide 39 and peptide 79 by ELISA. Cloning employed feeder cells as described above for subculturing. By these means, a cloned transformed human cell line was achieved which is continuous (immortal) and which secretes a human monoclonal antibody with the characteristics described above. In this example, the cell line and the antibody it produces carry the same designation.

Neutralization can be carried out by an alternate method. Culture supernatant was used after five-fold concentration with an Amicon-Centricon microconcentrator or unconcentrated. A dilution series was constructed with an initial 1:5 dilution followed by a two-fold dilution series using 25 ul of concentrated or unconcentrated culture supernatant diluted in medium (RPMI 1640, 15% fetal calf serum, 40% heat inactivated human serum). Virus ($1 \times 10^5$–$10^6$ tissue culture infectious units/ml) diluted 1:400 or 1:600 in medium was added to the constructed dilution series to a total volume of 50 ul. Samples were incubated for 45 minutes at 37° C. in a humidified chamber.

Infectivity was tested by the ability of the treated virus to infect MT-2 cells, an HTLV-I carrying cell line highly susceptible to LAV/HTLV-III infection. The MT-2 cells were plated in Costar flat bottom 96 well plate at $1 \times 10^5$ cells/well in 100 ul of medium. The plate was incubated for 45 minutes at 37° C. before the addition of 20 ul of the treated virus was added to each well. After 5–7 days the MT-2 cells were examined for syncytia formation which is indicative of LAV/HTLV-III infection.

I claim:

1. A human monoclonal antibody capable of reacting with an antigenic determinant of LAV/HTLV-III, wherein the human monoclonal antibody competes for the binding of an antibody produced by cell line ATCC No. CRL 9128.

2. A human monoclonal antibody that binds an epitope on the envelope glycoprotein gp41.

3. The human monoclonal antibody of claim 2 which binds to an epitope of the polypeptide encoded by pENV-3.

4. The human monoclonal antibody of claim 2 which binds to an epitope of peptide 39.

5. The human monoclonal antibody of claim 2 which binds an epitope of peptide 79.

6. An immortalized call line that produces human monoclonal antibody capable of reacting with an antigenic determinant of gp41 envelope protein of LAV/HTLV-III, wherein the cell line comprises B-lymphocyte cells capable of producing antibodies to an antigenic determinant of gp41 envelope protein of LAV/HTLV-III, transformed with Epstein-Barr virus transformed cells.

7. The cell line ATCC No. CRL 9128.

8. A monoclonal antibody produced by the cell line of claim 7.

9. The human monoclonal antibody of claim 1 tagged with a label capable of providing a detectable signal.

10. A method for determining the presence of LAV/HTLV-III in a biological sample comprising:
    incubating a human monoclonal antibody capable of reacting with an antigenic determinant of gp41 envelope protein of LAV/HTLV-III with a biological sample; and
    detecting the presence of immunecomplexes formed between said monoclonal antibody and said biological sample, and therefrom determining the presence of LAV/HTLV-III.

11. The method of claim 10 wherein said monoclonal antibody competes for the binding of an antibody produced by cellline ATCC No. CRL 9128.

12. The method of claim 10 wherein the monoclonal antibody binds an epitope on the envelope glycoprotein gp41.

13. The method of claim 10 wherein the monoclonal antibody is produced by the cell line ATCC No. CRL 9128.

14. The method of claim 10 wherein the monoclonal antibody is labeled.

15. The method of claim 14 wherein said label is selected from the group consisting of radionuclides, fluorescers, enzymes, enzyme substrates, enzyme cofactors, enzyme inhibitors, and ligands.

16. The method of claim 10 wherein the step of detection is by enzyme reaction, fluorescence, radioactivity, cell lysis, of luminescence emission.

17. The method of claim 10 wherein the biological sample is selected from the group consisting of bodily secretions, bodily fluids, and tissue specimens.

18. The human monoclonal antibody of claim 2, wherein the label is a fluorescer, enzyme, enzyme substrate, chemiluminescer, particle, or an antibody which bind to human antibodies.

* * * * *